(12) United States Patent
Fia et al.

(10) Patent No.: US 11,992,640 B2
(45) Date of Patent: May 28, 2024

(54) DEVICES FOR APPLYING A TOPICAL TREATMENT

(71) Applicant: THE JENEX CORPORATION, Toronto (CA)

(72) Inventors: Roberto Fia, Toronto (CA); Maurizio Battistuzzi, Toronto (CA)

(*) Notice: Subject to any disclaimer, the term of this patent is extended or adjusted under 35 U.S.C. 154(b) by 858 days.

(21) Appl. No.: 16/464,538

(22) PCT Filed: Nov. 28, 2017

(86) PCT No.: PCT/CA2017/051430
§ 371 (c)(1),
(2) Date: May 28, 2019

(87) PCT Pub. No.: WO2018/094540
PCT Pub. Date: May 31, 2018

(65) Prior Publication Data
US 2020/0384253 A1    Dec. 10, 2020

Related U.S. Application Data

(63) Continuation of application No. 15/787,599, filed on Oct. 18, 2017, now Pat. No. 11,344,707.
(Continued)

(30) Foreign Application Priority Data

Oct. 18, 2017    (CA) ................................ CA 2982914

(51) Int. Cl.
*A61M 37/00*    (2006.01)
*A61F 7/00*     (2006.01)
(Continued)

(52) U.S. Cl.
CPC ............. *A61M 37/00* (2013.01); *A61F 7/007* (2013.01); *A61K 33/38* (2013.01); *A61L 2/0023* (2013.01);
(Continued)

(58) Field of Classification Search
CPC .......... A61M 37/00; A61M 2037/0007; A61M 35/003
See application file for complete search history.

(56) References Cited

U.S. PATENT DOCUMENTS

| 4,090,517 A | 5/1978 | Takenaka |
| 4,291,685 A | 9/1981 | Taelman |

(Continued)

FOREIGN PATENT DOCUMENTS

| CN | 102429762 A | 5/2012 |
| DE | 3612622 A1 | 10/1987 |

(Continued)

OTHER PUBLICATIONS

International Search Report and Written Opinion regarding PCT/CA2017/051430, completed Feb. 28, 2018.
(Continued)

*Primary Examiner* — Catharine L Anderson
*Assistant Examiner* — Arjuna P Chatrathi
(74) *Attorney, Agent, or Firm* — Galvin Patent Law LLC; Brian R. Galvin

(57) ABSTRACT

A device comprising a housing having a handle end and a treatment end. The treatment end is configured to provide an antimicrobial treatment and a heat treatment. The treatment end comprises an applicator having an applicator surface for providing at least the heat treatment. The device includes a heat generation unit configured to heat the applicator surface in use, a source of antimicrobial agent, and a control unit operatively connected to at least the heat generation unit for
(Continued)

controlling the heat generation unit. The device can be a hand-held device and used to apply topical treatment to a treatment area of a subject.

16 Claims, 9 Drawing Sheets

Related U.S. Application Data

(60) Provisional application No. 62/426,889, filed on Nov. 28, 2016.

(51) Int. Cl.
| | | |
|---|---|---|
| *A61K 33/38* | (2006.01) | |
| *A61K 47/02* | (2006.01) | |
| *A61L 2/00* | (2006.01) | |
| *A61L 2/232* | (2006.01) | |
| *A61M 35/00* | (2006.01) | |
| *A61N 5/06* | (2006.01) | |
| *A61K 9/00* | (2006.01) | |
| *A61K 9/06* | (2006.01) | |
| *A61L 2/04* | (2006.01) | |
| *A61L 2/08* | (2006.01) | |
| *A61L 2/10* | (2006.01) | |

(52) U.S. Cl.
CPC ............ *A61L 2/0047* (2013.01); *A61L 2/0052* (2013.01); *A61L 2/0058* (2013.01); *A61L 2/0082* (2013.01); *A61L 2/232* (2013.01); *A61M 35/003* (2013.01); *A61N 5/0625* (2013.01); *A61K 9/0009* (2013.01); *A61K 9/0014* (2013.01); *A61K 9/06* (2013.01); *A61K 47/02* (2013.01); *A61L 2/04* (2013.01); *A61L 2/084* (2013.01); *A61L 2/085* (2013.01); *A61L 2/10* (2013.01); *A61L 2202/11* (2013.01); *A61L 2202/14* (2013.01); *A61L 2202/16* (2013.01); *A61M 2037/0007* (2013.01); *A61M 2205/8206* (2013.01); *A61N 5/0616* (2013.01); *A61N 5/0624* (2013.01); *A61N 2005/0651* (2013.01); *A61N 2005/0667* (2013.01)

(56) References Cited

U.S. PATENT DOCUMENTS

| | | | |
|---|---|---|---|
| 4,381,009 A | 4/1983 | Del | |
| 4,585,002 A | 4/1986 | Kissin | |
| 4,828,832 A * | 5/1989 | De Cuellar | A61K 33/38 424/618 |
| 4,860,748 A | 8/1989 | Chiurco et al. | |
| 4,944,297 A | 7/1990 | Ratkoff et al. | |
| 5,374,432 A * | 12/1994 | Fox, Jr. | A61K 33/38 514/184 |
| 5,445,146 A * | 8/1995 | Bellinger | A01M 1/02 606/3 |
| 5,470,585 A * | 11/1995 | Gilchrist | A61L 15/46 424/618 |
| 5,628,769 A | 5/1997 | Saringer | |
| 5,824,267 A * | 10/1998 | Kawasumi | A01N 25/34 424/618 |
| 5,830,211 A | 11/1998 | Santana et al. | |
| 6,066,164 A | 5/2000 | Macher et al. | |
| 6,475,211 B2 | 11/2002 | Chess et al. | |
| 6,645,531 B1 * | 11/2003 | Antelman | A61K 33/24 424/617 |
| 7,189,252 B2 | 3/2007 | Krueger | |
| 7,485,137 B2 | 2/2009 | Cheng | |
| 7,637,930 B2 | 12/2009 | Li et al. | |
| 7,749,260 B2 | 7/2010 | Da Silva et al. | |
| 7,871,427 B2 | 1/2011 | Dunbar et al. | |
| 8,066,854 B2 * | 11/2011 | Storey | C23C 14/325 204/298.41 |
| 8,182,475 B2 | 5/2012 | Conrad et al. | |
| 8,346,347 B2 | 1/2013 | Altshuler et al. | |
| 8,940,034 B2 | 1/2015 | Quisenberry | |
| 9,186,334 B2 | 11/2015 | Zhang et al. | |
| 9,364,649 B2 | 6/2016 | Park et al. | |
| 9,538,826 B2 | 1/2017 | Pires et al. | |
| 9,561,357 B2 | 2/2017 | Hall et al. | |
| 9,962,284 B2 | 5/2018 | Robinson et al. | |
| 10,085,879 B2 | 10/2018 | Pezzi | |
| 2002/0120262 A1 | 8/2002 | Bek et al. | |
| 2004/0224005 A1* | 11/2004 | Gabbay | A61F 6/04 424/443 |
| 2004/0243181 A1* | 12/2004 | Conrad | A61P 17/00 607/1 |
| 2007/0049998 A1 | 3/2007 | Conrad et al. | |
| 2007/0100403 A1 | 5/2007 | Felice et al. | |
| 2007/0233211 A1 | 10/2007 | Galer | |
| 2008/0031833 A1 | 2/2008 | Oblong et al. | |
| 2008/0063673 A1* | 3/2008 | Akridge | A61P 31/12 514/263.38 |
| 2008/0140164 A1 | 6/2008 | Oberreiter et al. | |
| 2010/0179623 A1 | 7/2010 | Hofer et al. | |
| 2010/0234925 A1 | 9/2010 | Harris et al. | |
| 2010/0292746 A1 | 11/2010 | Gorham | |
| 2011/0082415 A1 | 4/2011 | Ignon et al. | |
| 2011/0202048 A1 | 8/2011 | Nebrigic | |
| 2011/0245784 A1 | 10/2011 | Johnson | |
| 2012/0209357 A1 | 8/2012 | Ha | |
| 2013/0006154 A1 | 1/2013 | Lowe | |
| 2013/0006337 A1 | 1/2013 | Fernandes | |
| 2014/0200487 A1 | 7/2014 | Ramadas et al. | |
| 2014/0377318 A1 | 12/2014 | Cornell | |
| 2015/0032192 A1 | 1/2015 | Pezzi | |
| 2015/0366703 A1 | 12/2015 | Du | |
| 2016/0184162 A1* | 6/2016 | Grez | A46B 15/0028 601/18 |
| 2017/0021165 A1 | 1/2017 | Waldenburg | |
| 2017/0156664 A1 | 6/2017 | Belson et al. | |
| 2018/0369015 A1 | 12/2018 | Glucksman et al. | |

FOREIGN PATENT DOCUMENTS

| | | |
|---|---|---|
| DE | 19807453 A1 | 8/1999 |
| DE | 19853353 A1 | 6/2000 |
| DE | 19828910 A1 | 4/2001 |
| DE | 10134878 A1 | 2/2003 |
| DE | 202012100037 U1 | 2/2012 |
| DE | 202014104077 U1 | 9/2014 |
| DE | 202016001136 U1 | 9/2016 |
| EP | 1231875 B1 | 9/2004 |
| EP | 2716250 A2 | 4/2014 |
| EP | 2942041 A1 | 11/2015 |
| FR | 2660858 A1 | 10/1991 |
| FR | 2689002 A1 | 10/1993 |
| FR | 2720271 A1 | 12/1995 |
| IT | UA20164304 A1 | 8/2016 |
| JP | H10229995 A | 9/1998 |
| KR | 101226717 B1 | 1/2013 |
| WO | 2002064069 A2 | 8/2002 |
| WO | 2006076896 A1 | 7/2006 |
| WO | 2007082648 A1 | 7/2007 |
| WO | 2009023812 A1 | 2/2009 |
| WO | 2013149322 A1 | 10/2013 |

OTHER PUBLICATIONS

Supplementary Partial European Search Report issued in corresponding European patent application No. 1787499.6 dated Jun. 29, 2020.

PDF of webpage www.bite-away.com first retrieved on Oct. 23, 2017.

(56) References Cited

OTHER PUBLICATIONS

PDF of webpage www.itchstopper.com first retrieved on Oct. 23, 2017.

* cited by examiner

DEVICES FOR APPLYING A TOPICAL TREATMENT

CROSS-REFERENCE TO RELATED APPLICATIONS

This application is a U.S. National Stage Application under 35 U.S.C. § 371 of International Application No. PCT/CA2017/051430, filed Nov. 28, 2017, which is a continuation of U.S. application Ser. No. 15/787,599, filed Oct. 18, 2017, which claims benefit of priority from U.S. Provisional Application No. 62/426,889, filed Nov. 28, 2016, the contents of each of which are hereby incorporated by reference in their entireties.

TECHNICAL FIELD

The present technology relates to devices for applying a topical treatment, including but not limited to hand-held devices for applying a topical heat treatment.

BACKGROUND

Hand-held devices for delivering various topical treatments are known. One such device for delivering localized heat to treat cold sores is described in US 2007/0100403, and another device for pain suppression following insect bites is described in U.S. Pat. No. 4,944,297. The contents of both are incorporated herein by reference.

There is a need for an improved or an alternative device for providing topical treatment.

SUMMARY

It is an object of the present disclosure to provide a device for applying topical treatment, such as to a treatment area. The treatment area may be the skin of a user. The user may or may not be the operator of the device.

According to an aspect of the present technology, there is provided a device comprising: a housing having a handle end and a treatment end; the treatment end being configured to provide an antimicrobial treatment and a heat treatment, the treatment end comprising an applicator having an applicator surface for providing at least the heat treatment; a heat generation unit configured to heat the applicator surface in use; a source of antimicrobial agent; and a control unit operatively connected to at least the heat generation unit for controlling the heat generation unit. The device may be hand-held.

According to another aspect of the present technology, there is provided a hand-held device comprising an applicator for providing antimicrobial agents for topical application to a treatment area of a user, and a heat generation unit for heating the applicator and for providing topical heat to the treatment of the user. The device may further comprise a source of the antimicrobial agents, operatively connected to or forming at least a part of the applicator. The device may further comprise a control unit operatively connected to the heat generation unit. The applicator may comprise an applicator surface adapted for topical contact with the treatment area.

From another aspect, there is provided a hand-held device comprising an applicator having a silver coating for providing antimicrobial agents for topical application to a treatment area of a user, and a heat generation unit for heating the applicator and for providing topical heat to the treatment of the user. The topical application of the antimicrobial agents is substantially simultaneous to the topical heat treatment. The silver coating may have a thickness of about 1-10 microns, about 0.01-0.1 microns, about 0.1-1 microns, about 1-50 microns, about 1-45 microns, about 1-40 microns, about 1-35 microns, about 1-30 microns, about 1-25 microns, about 1-20 microns, or about 1-15 microns.

According to yet another aspect of the present technology, there is provided a hand-held device comprising a source of an antimicrobial agent for topical delivery of the antimicrobial agent to a treatment area of a user, a heat generation unit for providing heat to the treatment area in use, and a control unit for controlling both the topical delivery of the antimicrobial agent and the heat to the treatment area. In certain embodiments, the device further comprises an applicator having an applicator surface for the topical delivery of at least one of the antimicrobial agent and the heat.

In certain embodiments, the device and/or the control unit is configured to provide the heat treatment and the antimicrobial treatment substantially simultaneously. The heat treatment and the antimicrobial treatment may have substantially the same or different treatment times. In other embodiments, the heat treatment and the antimicrobial treatment are staggered or sequential.

In certain embodiments, the applicator surface is adapted for topical contact with the treatment area of the user. The treatment area may be the skin, nails or hair of a user.

In certain embodiments, the applicator surface comprises a heat conductive material. The heat conductive material may be formed on at least a part of the applicator or be integral with at least a part of the applicator. The source of antimicrobial agent may be a coating on the applicator or the applicator surface and/or incorporated in the applicator or the applicator surface. The source of antimicrobial agent may be a coating on a body of the applicator and/or incorporated in the body. Heating of the applicator surface and/or the applicator body may cause release of the antimicrobial agents. The source of antimicrobial agent may comprise a source of ions from a metal or a metal alloy, such as at least one of silver, copper, zinc, nickel, brass, and boron, or a source of particles. In other words, the antimicrobial agent, in certain embodiments, comprises silver, copper, zinc, nickel, or boron ions, or comprises silver, copper, zinc, nickel, or boron containing particles. In certain embodiments, the applicator surface comprises a silver coating on the applicator, the applicator being formed of a heat conductive metal. The silver coating may have a thickness of about 1-10 microns, about 0.01-0.1 microns, about 0.1-1 microns, about 1-50 microns, about 1-45 microns, about 1-40 microns, about 1-35 microns, about 1-30 microns, about 1-25 microns, about 1-20 microns, or about 1-15 microns.

In certain embodiments, at least a portion of the applicator surface comprises a mesh. The mesh may be formed of metal with an insulating coating on one side, such as made of a polymer.

In certain embodiments, the applicator has an opening formed therethrough and extending through the applicator surface. The opening may be used for allowing light transmission or dispensing of compositions such as antimicrobial agents.

In certain embodiments, the device includes a light source connectable to the control unit and arranged to emit light through the opening. In these embodiments, the device has a light pathway from the light source to the applicator surface or to another portion of the treatment end of the device. The light source may be configured to emit wavelength(s) within the visible range of the electromagnetic spectrum, for example one or more of the blue, green, orange, red and yellow parts of the electromagnetic spectrum. The light source may be configured to emit light having wavelength(s) within the ultraviolet range of the electromagnetic spectrum. The light source may be configured to emit light having wavelength(s) within the infrared range of the electromagnetic spectrum. The device may further include a lens for filtering the light emitted by the light source to emit a desired wavelength through the opening. Alternatively, the light source may be configured to emit the desired wavelength of light. Optionally, there may be provided a lens for focusing the light emitted by the light source. In certain embodiments, the heat generation unit includes the light source. The light source and the heat source may be the same. The heat generation unit may comprise a 1-1.5 W heater.

In certain embodiments, a surface area of the applicator surface is between about 20-40 mm$^2$, 30-40 mm$^2$, or about 35-40 mm$^2$. In certain embodiments, a surface area of the applicator surface is between about 40-250 mm$^2$, 40-200 mm$^2$, 40-150 mm$^2$, 40-100 mm$^2$, 150-250 mm$^2$, 175-250 mm$^2$, or 200-250 mm$^2$. Any other size of the applicator surface is possible and can be tailored to various uses.

The applicator surface may be circular in shape, or any other suitable shape or configuration.

In certain embodiments, the device further comprises a spacer positioned distally from the applicator surface for spacing the applicator surface from a treatment area of a user, the spacer comprising a rim made of an insulating material (e.g. a non-conductive material). The rim may be arranged to directly contact the treatment area of the user.

In certain embodiments, the housing has a cartridge port therein which is arranged to be connectable to a cartridge having a content therein. The cartridge port may be arranged to fluidly connect the content of the cartridge with an outlet at the treatment end of the device. The cartridge port and the cartridge may be provided with interchangeable connectors for connecting to each other, such as a male-female connector. The cartridge port is arranged to supply at least a portion of the content of the cartridge to the treatment end of the device in use. The outlet may be the opening extending through the applicator. In other words, the cartridge port may be fluidly connectable to the opening of the applicator in order to supply the content of the cartridge through the opening and to the applicator surface. Alternatively, the outlet may be separate from the applicator and the applicator surface and proximate the applicator and the applicator surface on the treatment end of the device.

The device may further comprise the cartridge. The content of the cartridge may comprise the source of the antimicrobial agent or the antimicrobial agent itself. The content of the cartridge may comprise an additional source of antimicrobial agent or the antimicrobial agent itself. The content may further comprise a carrier such as a gel, paste, emulsion or liquid. The content of the cartridge may also comprise at least one agent selected from an anti-inflammatory agent, an antibiotic agent, an anti-fungal agent, a skin soothing agent, a skin-rejuvenating agent, a heat-activatable agent, a wound healing agent, and a natural compound such as tea tree oil, oregano oil, a cannibanoid (e.g. tetrahyrdacanabinoids) etc. The content may comprise a source of ions from at least one of silver, copper, zinc, nickel, and boron in a liquid or gel suspension form, such as colloidal silver. One or both of the cartridge or the cartridge port may be operatively connected to the control unit and the control unit may be further configured to control the release of at least a portion of the content of the cartridge through the cartridge port. The control unit may be configured to release at least a portion of the contents of the cartridge from the cartridge port or the outlet at the same time as the applicator surface is caused to generate heat. The control unit may be configured to release at least a portion of the contents of the cartridge from the opening substantially simultaneously to the applicator surface being caused to generate heat.

In certain embodiments, the device further comprises a power source within the housing which is connectable to the control unit and/or the heat generation unit. The power source may be a battery which may be rechargeable. A charging base may be provided. In certain other embodiments, the power source may be external to the housing. The device may be provided with a power source connector for connecting to the external power source. The control unit may comprise a processor.

In certain embodiments, the control unit and/or heat generation unit is arranged to generate enough flux through the applicator surface to heat the treatment area (such as skin) adjacent the applicator surface up to a temperature tolerable by the user. The applicator surface, or the treatment area proximate the applicator surface, can heat up to about 40-65° C., 45-65° C., 50-65° C., 45-60° C., 45-55° C., 50-60° C., 50-55° C., 50-54° C., 55-65° C. or about 51-55° C. The applicator surface, or the treatment area proximate the applicator surface, can provide about 1-1.5 W of heat. The control unit includes a timer for controlling a time of heat and/or antimicrobial treatment. The heat treatment and/or the antimicrobial treatment comprises applying heat and/or antimicrobial treatment to the treatment area for between about 5-45 seconds, 5-40 seconds, 5-35 seconds, about 10-35 seconds, 20-35 seconds, 25-35 seconds, or about 30 seconds. In embodiments which include the light source, the timer is arranged to also control a light treatment from the light source.

In certain embodiments, the device further comprises a control interface (also called "user interface") on an outside of the housing which is connectable to the control unit. The control interface may comprise at least one button or at least one switch operatively connectable to the control unit. The control interface may comprise a display, which can be a touch screen.

In certain embodiments, the device further comprises a pressure sensor at the treatment end which is operatively connectable to the control unit and arranged to start or end a time of the antimicrobial treatment and the heat treatment when a predetermined pressure is detected, a predetermined pressure change is detected, or a predetermined time has lapsed. A cover may be provided over the pressure to avoid inadvertent action.

In certain embodiments, the device further comprises an actuator for delivering negative or positive pressure to the treatment area. The applied pressure may be a vibration, which can have a range of amplitudes and a range of frequencies.

In certain embodiments, the device further comprises at least one biological sensor at, or proximate to, the treatment end and/or the applicator surface for detecting a biological condition such as a pathogen (e.g. virus, bacteria, fungus). In certain embodiments, the device further comprises at least one environmental sensor for detecting an environmental condition such as temperature, humidity, pollution levels, pollen levels, pressure, wind speed, etc.

The at least one biological sensor and/or the at least one environmental sensor may be connectable to the control unit which is arranged to select an appropriate heat and/or antimicrobial treatment time and/or intensity according to the detected biological and/or environmental condition.

In certain embodiments, the device is a connected device and comprises a receiver for receiving signals and/or a transmitter for transmitting signals. The receiver and/or transmitter may be operatively connected to the control unit. The signals may be any type of signal used in communication, such as radio waves or microwaves, and the device may be connectable to an internet network or to other devices by WIFI, Bluetooth™ and/or other wireless communication standards. In certain embodiments, the control unit is arranged to select an appropriate heat and/or antimicrobial treatment time and/or intensity according to information concerning a geographical location received by the receiver.

In certain embodiments, the device further comprises a Global Positioning System (GPS). The device may also include an indicator for indicating to a user of the device when the device is in a geographical location which is at high risk of Zika virus or West Nile virus infection.

In certain embodiments, the applicator surface or the applicator is detachably attachable or removeably connectable to the device. The applicator surface or the applicator can be replaceable. Optionally, the detachably attachable applicator comprises an applicator surface which is a silver coating. The silver coating may have a thickness of about 1-10 microns, about 0.01-0.1 microns, about 0.1-1 microns, about 1-50 microns, about 1-45 microns, about 1-40 microns, about 1-35 microns, about 1-30 microns, about 1-25 microns, about 1-20 microns, or about 1-15 microns. Attachment of the applicator or the applicator surface to the device can be by any attachment mechanism such as a screw connection, a clip, a clasp, or the like. In one embodiment, attachment of the applicator or applicator surface is achieved by means of using materials having different coefficients of expansion to ensure a more secure fit when the applicator or applicator surface is heated.

In certain embodiments, the device further comprises an applicator connector having a base portion arranged to be retained in the housing, and an extender portion arranged to extend from the base portion at the treatment end, the extender portion being detachably connectable to the applicator.

In certain embodiments, the heat generation unit is a heating plate operatively connectable to the control unit and operatively connectable to the applicator.

In certain embodiments, the device further comprises a thermal sensor proximate the heat generation unit, the thermal sensor being operatively connected to the control unit.

In certain embodiments, the device further comprises an activator unit for activating the control unit when operatively connected thereto, the activator unit comprising a body which is connectable to the housing and having at least one electrical connector extending from the body and arranged to operatively connect to the control unit; and instructions for instructing the control unit to allow use of the device for a pre-determined number of rounds of treatment or for a pre-determined time period. The instructions are computer readable.

From another aspect, there is provided a device comprising a control unit for controlling administration of a treatment from a treatment end of the device, and an activator unit for activating the control unit when operatively connected thereto, the activator unit comprising computer readable instructions for activating the control unit to allow administration of the treatment from the device. The treatment may comprise a pre-determined number of rounds of treatment or a pre-determined time period. The activator unit may have a body which is detachably attachable to the device, and operatively connectable to the control unit. The body may comprise at least one electrical connector extending from the body and arranged to operatively connect to the control unit. The activator unit may be pre-loaded with a predefined extent of administration of treatment, such as a predefined of number of rounds of treatment or a predetermined time period. Alternatively, additional treatment extents may be charged to the activator unit.

From another aspect, there is provided a kit comprising a device as described above and at least one cartridge. The cartridge may comprise a cartridge housing having a connector end, the connector end being configured to fluidly connect with the cartridge port of the device. The connector end may be arranged to open when fluidly connected to the cartridge port of the device to allow flow of the content of the cartridge into the cartridge port. The content of the cartridge may comprise a source of ions from at least one of silver, copper, zinc, nickel, and boron in a liquid or gel suspension form, such as colloidal silver, and/or at least one agent selected from an anti-inflammatory agent, an antibiotic agent, a skin soothing agent, a heat-activatable agent, a wound healing agent, a natural compounds such as tea tree oil, oregano oil, a cannibanoid (e.g. tetrahyrdacanabinoids), etc.

From another aspect, there is provided a kit comprising a device as described above and at least one detachably attachable applicator or applicator surface. The kit may include a plurality of applicators or applicator surfaces which can be detachably attachable to the device. The applicators or applicator surfaces may be the same as one another, or have different properties in terms of size, shape, material, coating etc. Each applicator may comprise a body and an applicator surface for applying at least one of a heat treatment and antimicrobial treatment. The applicator surface may comprise a silver coating. The silver coating may have a thickness of about 1-10 microns, about 0.01-0.1 microns, about 0.1-1 microns, about 1-50 microns, about 1-45 microns, about 1-40 microns, about 1-35 microns, about 1-30 microns, about 1-25 microns, about 1-20 microns, or about 1-15 microns. The applicator body may comprise a metal alloy different from that of the applicator surface. The applicator body has an opening extending therethrough. In one embodiment, the kit comprises the device as described above and at least two removeably attachable applicators, each applicator in the form of a tip and having an applicator surface comprising a silver coating. In this embodiment, the applicator surfaces of the applicators have a different surface area from one another.

From another aspect, there is provided a cartridge for use with any of the aspects or embodiments of the device described herein, wherein the cartridge comprises a cartridge housing having a connector end, the connector end being configured to fluidly connect with the cartridge port of the device. The connector end may be arranged to open when fluidly connected to the cartridge port of the device to allow flow of the content of the cartridge into the cartridge port. The content of the cartridge may comprise a source of ions from at least one of silver, copper, zinc, nickel, and boron in a liquid or gel suspension form. The content of the cartridge may comprise at least one agent selected from an anti-inflammatory agent, an antibiotic agent, an antiviral agent, an antifungal agent, a skin soothing agent, a cooling agent, a heat-activatable agent, a wound healing agent, and a skin rejuvenating agent.

From another aspect, there is provided use of heat (thermal energy) and an antimicrobial agent to kill or inactivate a virus. The heat treatment and antimicrobial treatment may be effected by applying a heated source of antimicrobial agents to an environment containing the virus. The virus may comprise the Zika virus, the herpes simplex virus, and/or the West Nile virus. Other virus's are also possible. The antimicrobial agent may comprise silver and/or copper ions and/or particles. The heat treatment may comprise heating to a temperature of between 45-65° C., 50-60° C., or about 51-55° C. The heat treatment may comprise heating to a temperature of less than about 56° C., or less than about 55° C. The heat treatment may comprise applying heat from a 1-1.5 W heater. Thermal energy up to 1.3 W can be used. The heat treatment and/or the antimicrobial treatment may have a treatment time of about 3-15 seconds, about 10-15 seconds, about 5-35 seconds, about 10-35 seconds, about 20-35 seconds, about 25-35 seconds, about 5 seconds, about 10 seconds, about 15 seconds, about 20 seconds, about 25 seconds, about 30 seconds, about 35 seconds, about 40 seconds, about 45 seconds, about 50 seconds, about 55 seconds or about 60 seconds. The use may further comprise light treatment within the ultraviolet, infrared and/or visible range of the electromagnetic spectrum.

From another aspect, there is provided use of heat, light (e.g. within the visible, ultraviolet and/or infrared range of the electromagnetic spectrum) and silver and/or copper ions to kill or inactivate the Zika virus and/or the West Nile virus. From another aspect, there is provided use of silver or copper ions or particles to kill or inactivate the Zika virus and/or the West Nile virus and/or the Dengue virus.

From a further aspect, there is provided use of a heated silver surface for topically treating a viral infection.

From another aspect, there is provided a method of topically killing or inactivating a virus comprising topically applying a heat treatment and an antimicrobial agent to a treatment area of a patient. The heat treatment and antimicrobial treatment may comprise applying a heated source of antimicrobial agents to an environment containing the virus. The virus may comprise the Zika virus, the Dengue virus, the herpes simplex virus, and/or the West Nile virus. Other virus's are also possible. The antimicrobial agent may comprise silver and/or copper ions and/or particles. The method may comprise use of silver or copper ions or particles to kill or inactivate the Zika virus and/or the West Nile virus. The heat treatment may comprise heating to a temperature of between 45-65° C., 50-60° C., or about 51-55° C. The heat treatment may comprise heating to a temperature of less than about 56° C., or less than about 55° C. The heat treatment and/or the antimicrobial treatment may have a treatment time of about 3-15 seconds, about 10-15 seconds, about 5-35 seconds, about 10-35 seconds, about 20-35 seconds, about 25-35 seconds, about 5 seconds, about 10 seconds, about 15 seconds, about 20 seconds, about 25 seconds, about 30 seconds, about 35 seconds, about 40 seconds, about 45 seconds, about 50 seconds, about 55 seconds or about 60 seconds. The method may further comprise light treatment within the ultraviolet, infrared and/or visible range of the electromagnetic spectrum.

From a yet further aspect, there is provided a method of topically treating a viral infection by applying a heated silver surface for a treatment time. From a further aspect, there is provided a method of treating Zika virus infection comprising topically applying on an insect bite a heated silver surface for a treatment time. In certain embodiments, the heated silver surface has a temperature of between about 45-65° C., about 50-60° C., about 50-55° C., 50-54° C., 50-53° C., 50-52° C., or about 51-55° C. In certain embodiments, the treatment time is about 3-15 seconds, about 10-15 seconds, about 5-35 seconds, about 10-35 seconds, about 20-35 seconds, or about 25-35 seconds. In certain embodiments, the heated silver surface is applied more than once, with a rest interval inbetween. The rest interval can be up to 5 minutes. In certain embodiments, the rest interval is between about 10-20 seconds, about 20-30 seconds, about 30-40 seconds, about 40-50 seconds, about 50-60 seconds, about 1-2 minutes, about 2-3 minutes, about 3-4 minutes, about 4-5 minutes. In certain embodiments, the heated silver surface comprises the applicator surface of the device as described above.

The heat treatment and the antimicrobial treatment may be applied for a time and an intensity sufficient to inactivate the virus topically. The heat treatment and the antimicrobial treatment may be applied within 6 hours, 5 hours, 4 hours, 3 hours, 2 hours or 1 hour of receiving a virus infected insect-bite.

Advantageously, the topical application of heat and an antimicrobial agent, such as silver ions or copper ions, was found by the inventors to have a synergistic effect. In certain embodiments, heating of the applicator coated with the source of the antimicrobial agent and contacting the treatment area with the applicator surface providing the heat and the antimicrobial agent had a synergistic treatment effect on the treatment area.

Embodiments of the present technology each have at least one of the above-mentioned object and/or aspects, but do not necessarily have all of them. It should be understood that some aspects of the present technology that have resulted from attempting to attain the above-mentioned object may not satisfy this object and/or may satisfy other objects not specifically recited herein.

It must be noted that, as used in this specification and the appended claims, the singular form "a", "an" and "the" include plural referents unless the context clearly dictates otherwise.

As used herein, the term "about" in the context of a given value or range refers to a value or range that is within 20%, preferably within 10%, and more preferably within 5% of the given value or range.

As used herein, the term "and/or" is to be taken as specific disclosure of each of the two specified features or components with or without the other. For example "A and/or B" is to be taken as specific disclosure of each of (i) A, (ii) B and (iii) A and B, just as if each is set out individually herein.

As used herein, the term "antimicrobial agent" is used broadly and includes agents which may be any one or more of antiviral, antifungal and antibacterial, or any other agent which is able to inactivate pathogens or prevent a pathogen infection. Pathogens include bacteria, and virus's such as Zika, Dengue, West Nile, and Herpes Simplex.

Additional and/or alternative features, aspects, and advantages of embodiments of the present technology will become apparent from the following description, the accompanying drawings, and the appended claims.

BRIEF DESCRIPTION OF THE DRAWINGS

For a better understanding of the present technology, as well as other aspects and further features thereof, reference is made to the following description which is to be used in conjunction with the accompanying drawings, where.

DETAILED DESCRIPTION

A device will be described with respect to delivery of heat and antimicrobial agents. Broadly, there is provided a device 10 for providing delivery of heat and antimicrobial agents for topical treatment to a treatment area of a user. Embodiments of the device 10 can also deliver light and other treatments such as negative or positive pressure, vibration, and cooling. The device 10 can be used for applying any one or more of antibacterial agents, antiviral agents, antifungal agents, soothing agents, healing agents, skin rejuvenating agents, heat/light activatable agents, and anti-inflammatory agents on the treatment areas of the user, including but not limited to intact skin, compromised skin, wounds, sores, hair, nails, or insect bites or animal bites.

Figure 1:
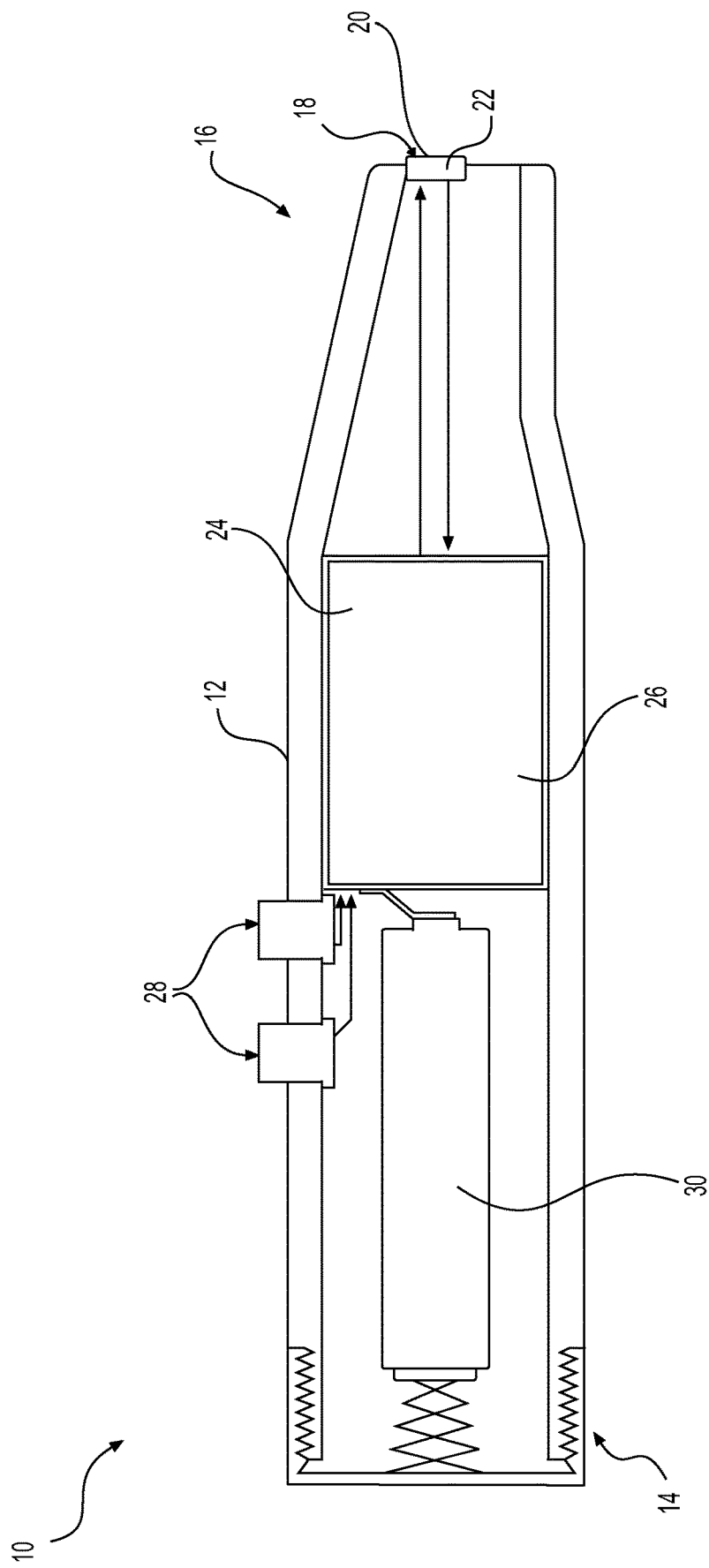
FIG. 1 is a longitudinal cross-sectional view of a device according to an embodiment of the present disclosure.

Referring to a first embodiment shown in FIG. 1, the device 10 is sized and shaped to be hand-held and comprises a housing 12 having a handle end 14 and a treatment end 16. The treatment end 16 is configured to provide the antimicrobial treatment and the heat treatment to the treatment area, which in this embodiment is the skin of a user at a site of an insect bite. An applicator 18 is provided at the treatment end 16 and comprises an applicator surface 20 for transferring heat to provide the heat treatment. The applicator surface 20 is arranged to contact the treatment area in use, and is appropriately sized and shaped for the use. In this embodiment, the applicator surface 20 provides a source of antimicrobial agent for the antimicrobial treatment, which will be explained further below. The applicator surface 20 is on an outwardly facing side of the applicator 18 and arranged to contact the treatment area of the user. The applicator 18 comprises a body 22 made at least partially of a heat conductive material.

The device 10 includes a heat generation unit 24, operatively connected to the applicator surface 20 through the applicator body 22 and configured to heat the applicator surface 20 in use. A control unit 26 is also provided which is operatively connected to the heat generation unit 24 for modulating the intensity and/or timing of the heat and/or antimicrobial treatment. In this embodiment, the heat generation unit 24 and the control unit 26 are illustrated as being a single unit. In other embodiments, the heat generation unit 24 and the control unit are separate components.

Buttons 28 are provided on an outside of the housing 12, for engagement with a user's fingers, and which are operatively connected to the control unit 26 to provide an input to the control unit 26 to select or control the heat and/or antimicrobial treatment. It will be appreciated that the heat treatment and the antimicrobial treatment are not necessarily generated or applied at the same time. They may be sequentially applied or in an overlapping fashion. Instead of, or in addition to, buttons 28, the device 10 can be provided with any other type of control means or control interface such as a touch screen or switches (not shown).

The device 10 includes a power source 30, such as a battery 30, which provides power to the control unit 26 and the heat generation unit 24. The buttons 28 are also operatively connectable to the battery 30 to enable a user to power on and off the device 10, as well as to control the treatment.

The applicator body 22 is made of a metal. The applicator surface 20 comprises a coating 20 on the body 22 of the applicator 18. In this embodiment, the applicator body 22 is made of an aluminium alloy and the applicator surface 20 comprises a coating of silver. In other embodiments, the material of the applicator body 22 is chosen to further accentuate a galvanic effect of the silver coating on the applicator body. The silver coating has a thickness of about 1-10 microns. In other embodiments, the coating thickness is about 0.01-0.1 microns, 0.1-1 microns, 1-50 microns, about 1-45 microns, about 1-40 microns, about 1-35 microns, about 1-30 microns, about 1-25 microns, about 1-20 microns, or about 1-15 microns. The silver coating comprises more than about 95% silver, such as 99% silver. The silver coating comprises the source of the antimicrobial agent. In this case, the antimicrobial agent comprises antimicrobial ions and/or particles which are applied onto the user's skin when the applicator surface 20 contacts the user's skin. Heating the silver coating, such as by means of the heat generation unit 24, is thought to facilitate the release of the antimicrobial agents from the silver coating.

In other embodiments, in addition to, or instead of, the silver coating, the applicator surface 20 may be made of any other material. Alternatively, the applicator surface 20 and the applicator body 22 may be made of the same material. The applicator surface 20 and/or the applicator body 22 may be doped with a silver compound. Instead of silver, any other material can be used as the applicator surface 20 and/or the applicator body 22 which can provide an antimicrobial, antibacterial, antiviral, antifungal effect, anti-inflammatory or soothing, such as copper, zinc, nickel, gallium, titanium dioxide, magnesium oxide compounds and alloys.

At least a portion of the treatment end 16 is arranged to contact the treatment area to deliver heat and the antimicrobial agent. In the embodiment of FIG. 1, it is the applicator surface 20 alone which is arranged to contact the user's skin. In other embodiments (not shown), other portions of the treatment end 16 may also be arranged to contact the treatment area of the user.

In this embodiment of the device 10, for the treatment of insect bites, the applicator surface 20 has a surface area of about 240 $mm^2$.

In other embodiments, the size of the applicator surface 20 can be adapted according to the intended use of the device 10. Any other shape or size of the applicator surface 20 are possible and can be tailored to various uses. For example, the applicator surface 20 can have a surface area of between about 20-40 $mm^2$, 30-40 $mm^2$, or about 35-40 $mm^2$. In yet other embodiments, the applicator surface 20 has a surface area of about 40-250 $mm^2$, 40-200 $mm^2$, 40-150 $mm^2$, 40-100 $mm^2$, 150-250 $mm^2$, 175-250 $mm^2$, or 200-250 $mm^2$.

In certain other embodiments (not shown) the applicator 18 comprises a metal mesh with a polymer coating on the side facing away from the applicator surface 20. The applicator 18 and the applicator surface 20 can take any other configuration according to the desired use. In certain other embodiments (shown in FIGS. 4-9), the applicator 18 is removeably attachable from the treatment end 16 of the device 10.

The heat generation unit 24 comprises a controllable heat source for generating heat. The heat generation unit 24 is arranged to generate enough flux to heat the applicator surface 20 to about 40-65° C., 45-65° C., 50-65° C., 45-60° C., 45-55° C., 50-60° C., 50-55° C., 55-65° C. or about 51-55° C. The heat generation unit 24 comprises a circuit connected to the power source 30. In other embodiments, the heat can be generated in any other way using for example a light bulb (not shown), or any other suitable apparatus.

The control unit 26 includes a timer (not shown) for controlling a time of heat and/or antimicrobial treatment. For example, the control unit 26 has a processor and controls the switching on and off of the heat generation unit 24. In certain embodiments, the control unit 26 is pre-programmed with predetermined treatment programs having different treatment times and/or intensities. A treatment program may comprise a different heat treatment time compared to a different antimicrobial treatment time. The heat and antimicrobial treatments may be applied consecutively, simultaneously, or may overlap. A suitable treatment program is selected by a user through the buttons 28. The treatment program may comprise more than one application of heat and/or antimicrobial application. Multiple applications of lower temperature heat in conjunction with a synergistic treatment are preferred in some embodiments as they are better tolerated by the user and as effective as higher temperature treatments.

In certain embodiments, the device 10 includes a safety cut-off mechanism to ensure that the applicator surface 20 does not exceed an upper temperature that is considered safe, or that the applicator surface 20 does not remain at a treatment temperature for longer than a predetermined time that is considered safe. The safety cut-off mechanism can include a thermal sensor (shown in FIG. 5) connected to the control unit 26 such that the control unit 26 turns off the heat once a predetermined threshold temperature has been reached.

In certain embodiments, the control unit 26 includes a receiver (not shown) for receiving signals and/or a transmitter (not shown) for transmitting signals, such as radio signals. The receiver and/or transmitter are operatively connected to the control unit 26. In these embodiments, the device 10 is connectable to the internet or to other devices, such as using Bluetooth™. In certain embodiments, the control unit 26 is arranged to select an appropriate treatment program according to information received from the receiver. This information may be based on the geographical location of the device 10 and on likelihood of infection from various insect-borne diseases such as Zika virus, West Nile virus, malaria, etc. In this respect, the device 10 may include a GPS receiver (not shown).

In certain embodiments, the device 10 includes one or more sensors for providing data input to the control unit 26 which may also be used to select an appropriate treatment program. One or more biological and/or environmental sensors (not shown) are included in the device 10. Biological sensors sense a condition of the user's tissue or body (such as a temperature, a virus, a bacteria, a fungus, a hormone, a protein or any other biological marker), and environmental sensors measure environmental conditions such as one or more of air temperature, humidity, pressure, pollution, and pollen. For example, a biological sensor detects the Zika virus through an insect bite on a user's skin. On detection of the Zika virus, the control unit 26 selects and applies the appropriate treatment program.

Predefined data specifying the suitable treatment program for various conditions may be accessed by the control unit 26 to determine the suitable treatment program. In certain embodiments, the data is stored in a memory (not shown) of the control unit 26. In other embodiments, the data is stored externally to the device 10, but accessible by the device 10, such as on a server.

In certain embodiments, the device 10 includes a display screen (not shown) for displaying treatment program options to the user or for displaying measured or detected conditions.

Figure 2:
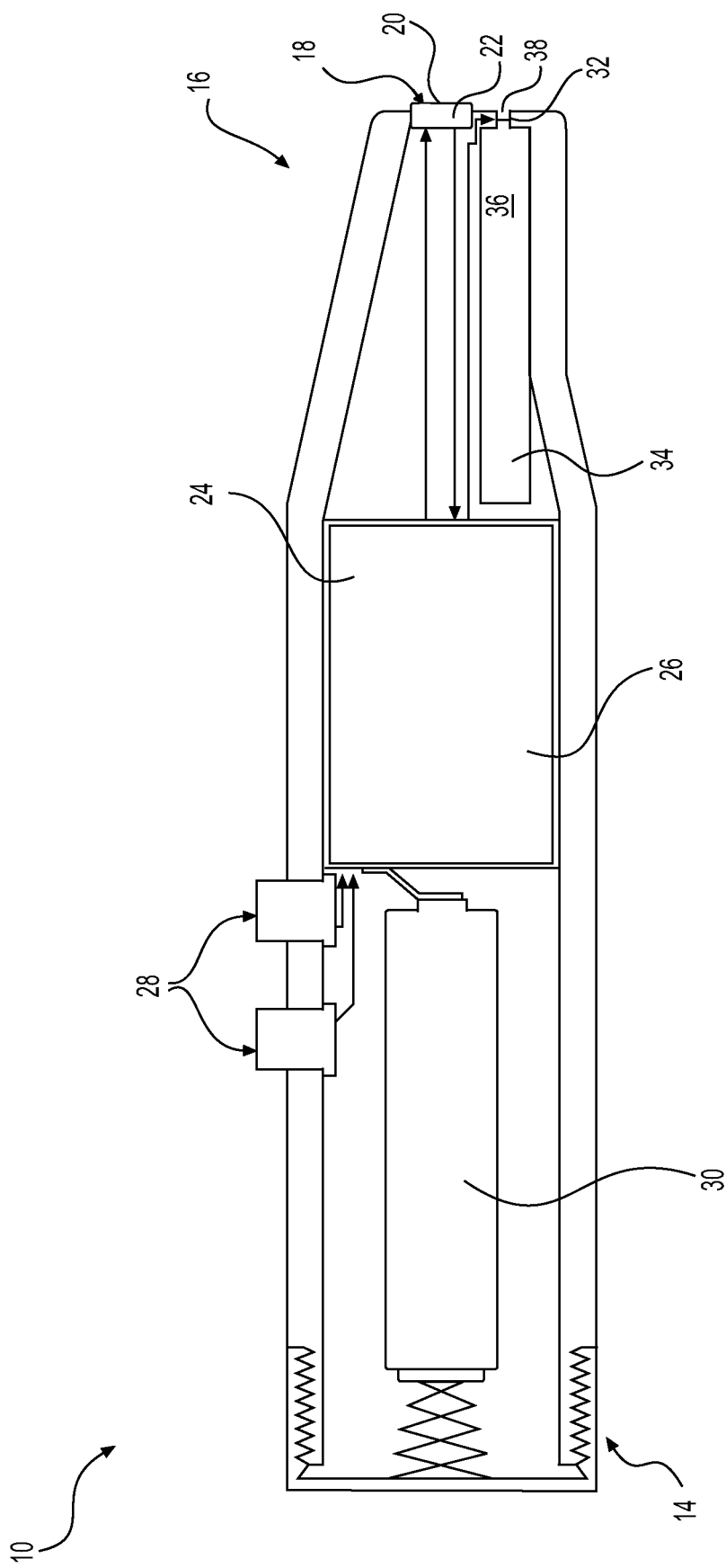
FIG. 2 is a longitudinal cross-sectional view of another embodiment of the device of the present disclosure.

Referring now to FIG. 2, the embodiment of the device 10 of FIG. 2 differs from that of FIG. 1 in that there is also provided a cartridge port 32 in the housing 12 which is connectable to a cartridge 34 having a content 36 therein. The cartridge port 32 is arranged to supply at least a portion of the content 36 of the cartridge 34 to an outlet in the treatment end 16 in use. The outlet is the opening 38. As can be seen, the opening 38 is separate from the applicator surface 20 but proximate thereto. The outlet can be provided elsewhere on the device, for example in the applicator 18 (as seen in the embodiments of FIG. 3, and FIGS. 4-9).

In this embodiment, the cartridge 34 comprises the source of the antimicrobial agent for the antimicrobial treatment instead of the applicator surface 20. In certain other embodiments (see for example FIGS. 4-9), the applicator surface 20 provides the antimicrobial agent source.

The cartridge content 36 comprises a source of silver ions or particles, such as colloidal or ionised silver. Alternatively, the content 36 of the cartridge 34 may comprise any other source of metal particles or ions. The antimicrobial agent comprises a liquid, gel, emulsion or paste carrier. Some examples of such agents include a source of copper, zinc, nickel, or boron.

In alternative embodiments, the content 36 of the cartridge 34 comprises at least one agent selected from an anti-inflammatory agent, an antibiotic agent, an antiviral agent, an antifungal agent, a skin soothing agent, a cooling agent, a heat-activatable agent, a wound healing agent, and a skin rejuvenating agent. The agent may be a natural compound or an essential oil and include actives such as tea tree extract, lavender, oregano, frankincense, clove, cinnamon, apple cider vinegar, medical marijuana (oil or other form), hemp, cannabidiol, tetrahyrdacanabinoids, camomile, aloe vera, or the like. These agents can be in any suitable carrier such as grapeseed oil, jojoba oil, castor oil, almond oil, gels, pastes, solutions, suspensions, or the like. In some embodiments, these agents have a complementary effect to the heat treatment from the applicator surface 20.

In certain other embodiments, such as those in which the antimicrobial agent is delivered by the cartridge 34, the treatment end 16 is adapted so that the heatable applicator surface 20 does not contact the user's skin. In this case, a spacer (not shown) is provided on the applicator surface 20 which will contact the user's skin and space the applicator surface 20 from the user's skin to apply radiant heat. The spacer comprises a rim of non-conductive material. The applicator surface 20 and the rim are circular. In these embodiments, an upper temperature of the applicator surface 20 is higher than an upper temperature of the applicator surface 20 of FIG. 1.

The cartridge port 32 is selectively operable, by means of a valve (not shown), to allow fluid flow from the cartridge 34 to the opening 38. In this respect, the cartridge port 32 is operatively connected to the control unit 26. The control unit 26 is configured to separately control the heat generation unit 24 and the cartridge port 32. In other embodiments, the cartridge port 32 is selectively operable by means of applying pressure or other mechanical means to actuate the valve.

In certain embodiments, the device 10 is provided as part of a kit including the cartridge 34. The kit can include one or more additional cartridges 34 including the same or different contents 36.

Figure 3:
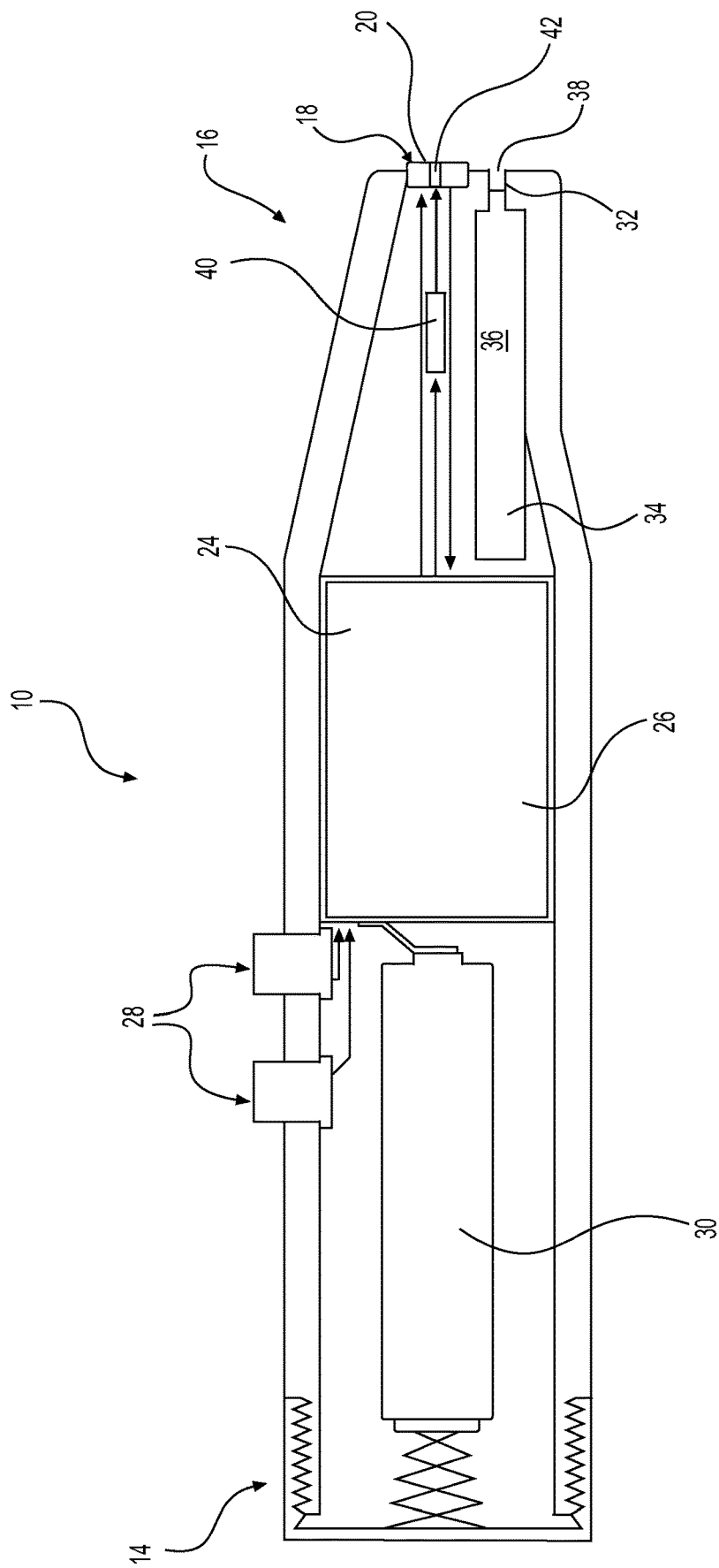
FIG. 3 is a longitudinal cross-sectional view of yet another embodiment of the device of the present disclosure.
Figure 4:
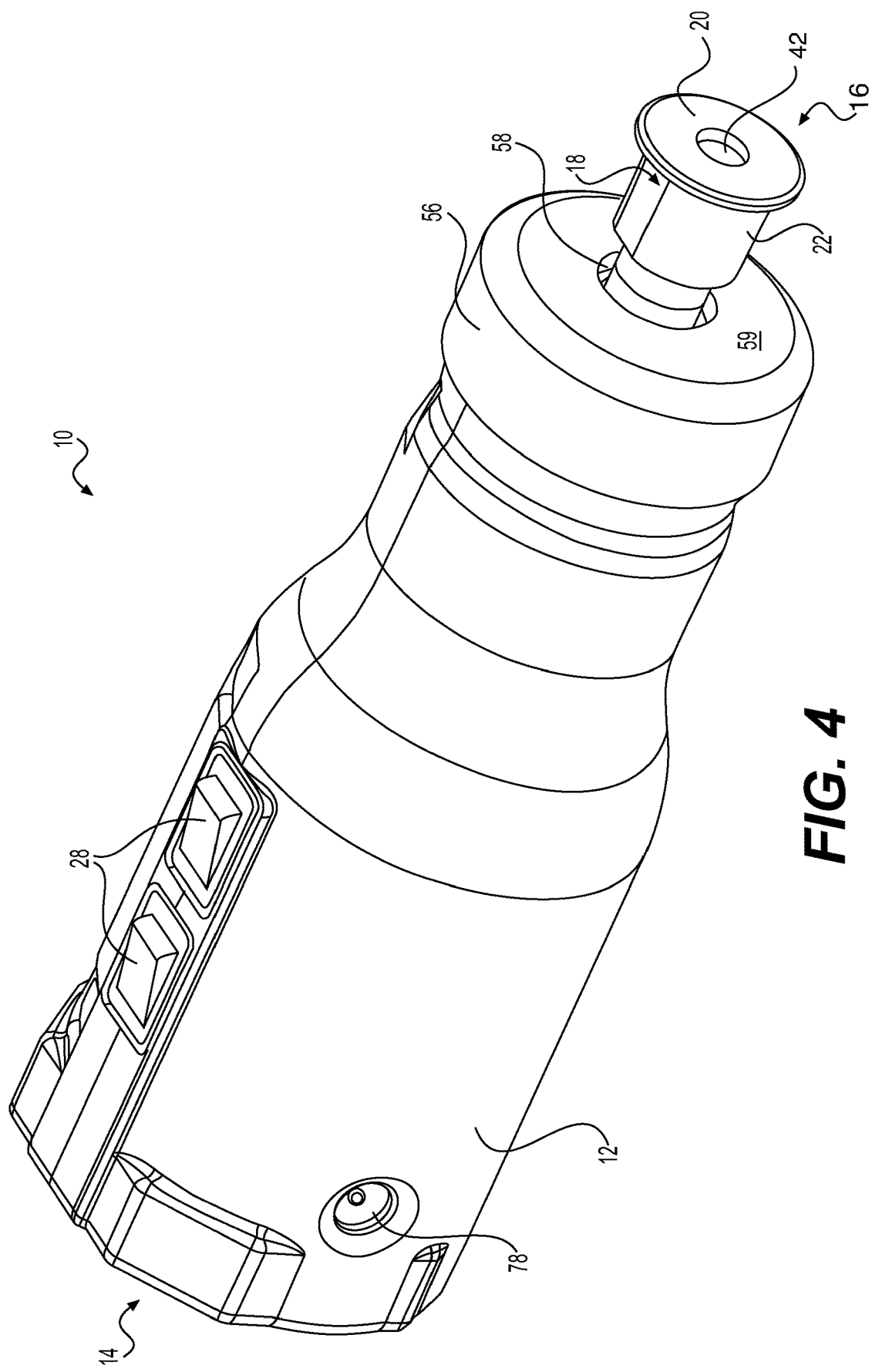
FIG. 4 is a perspective view of a further embodiment of the device according to the present disclosure.
Figure 5:
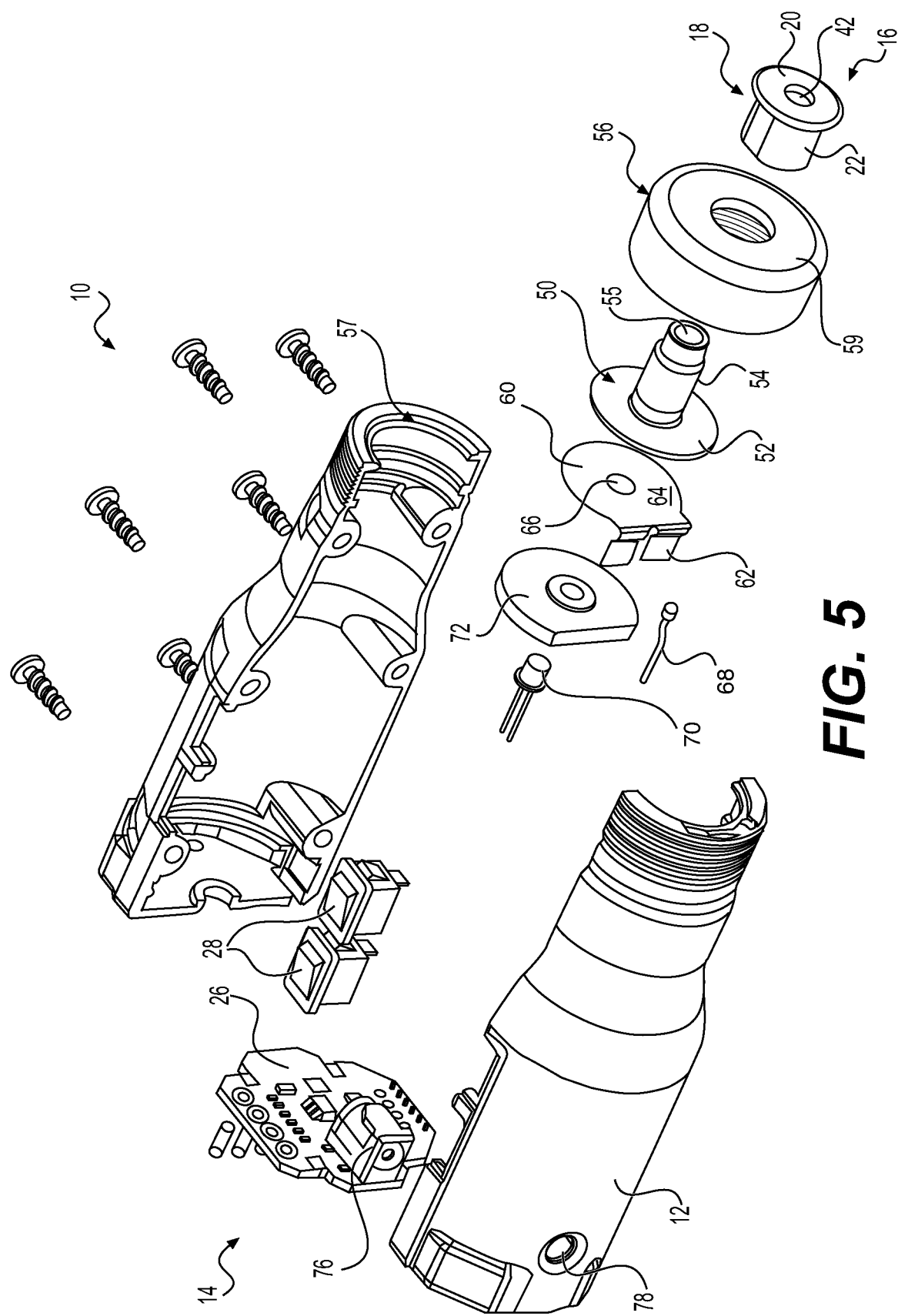
FIG. 5 is an exploded view of the device of FIG. 4.
Figure 6:
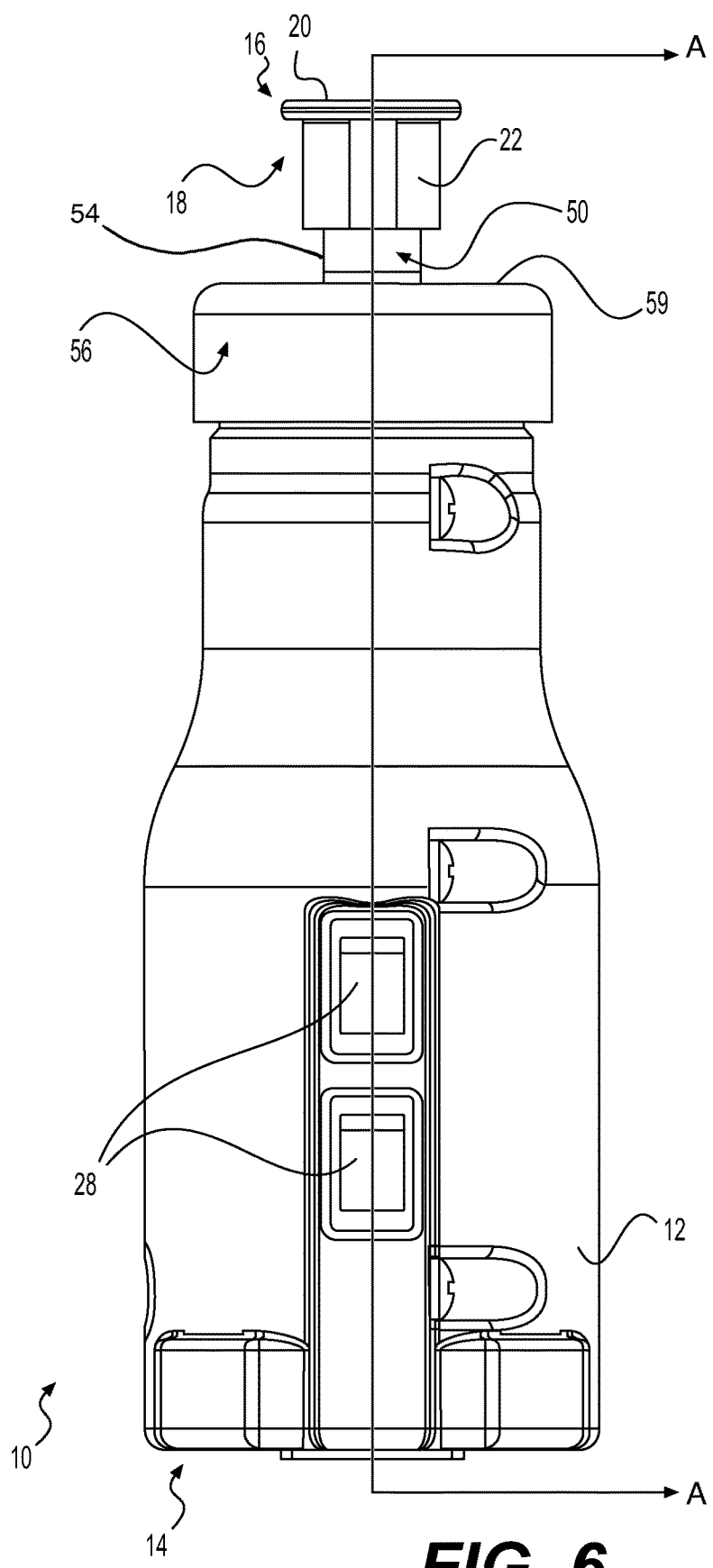
FIG. 6 is a top plan view of the device of FIG. 4.
Figure 7:
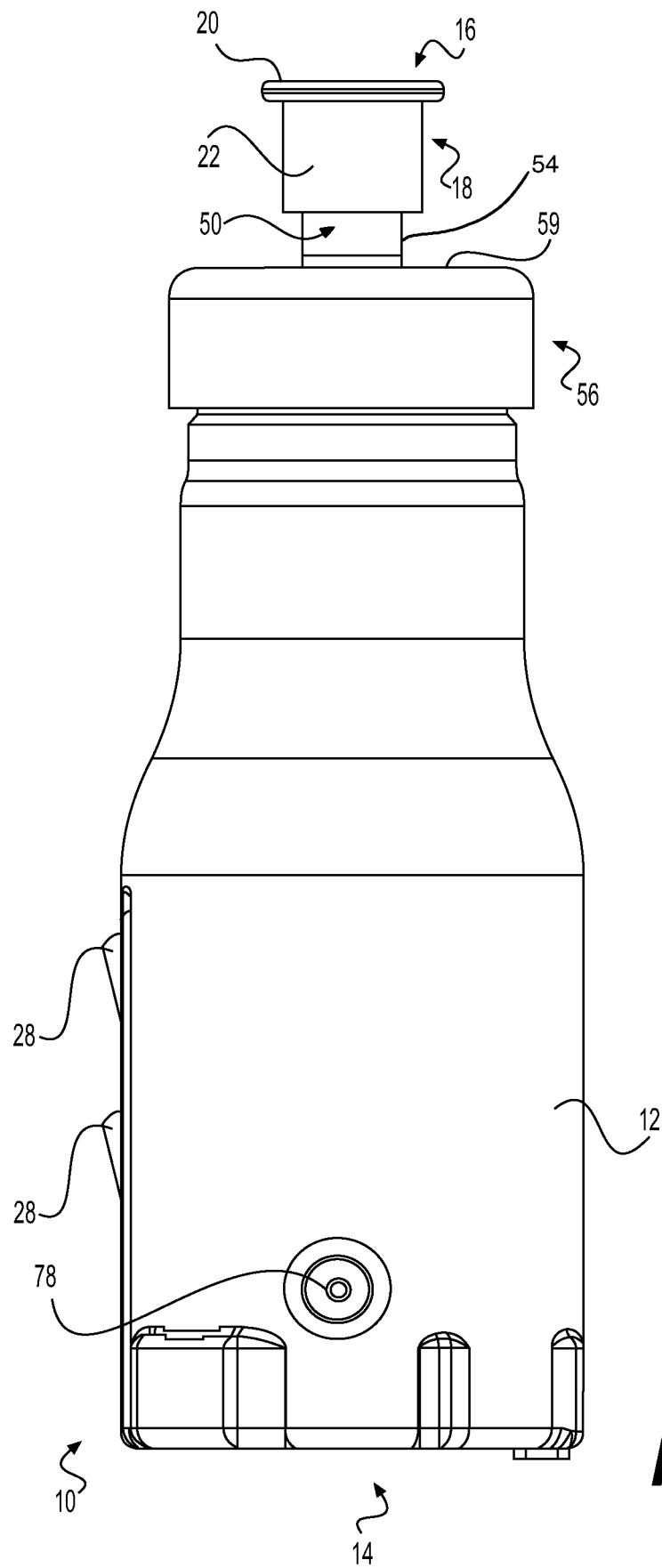
FIG. 7 is a side view of the device of FIG. 4.
Figure 8:
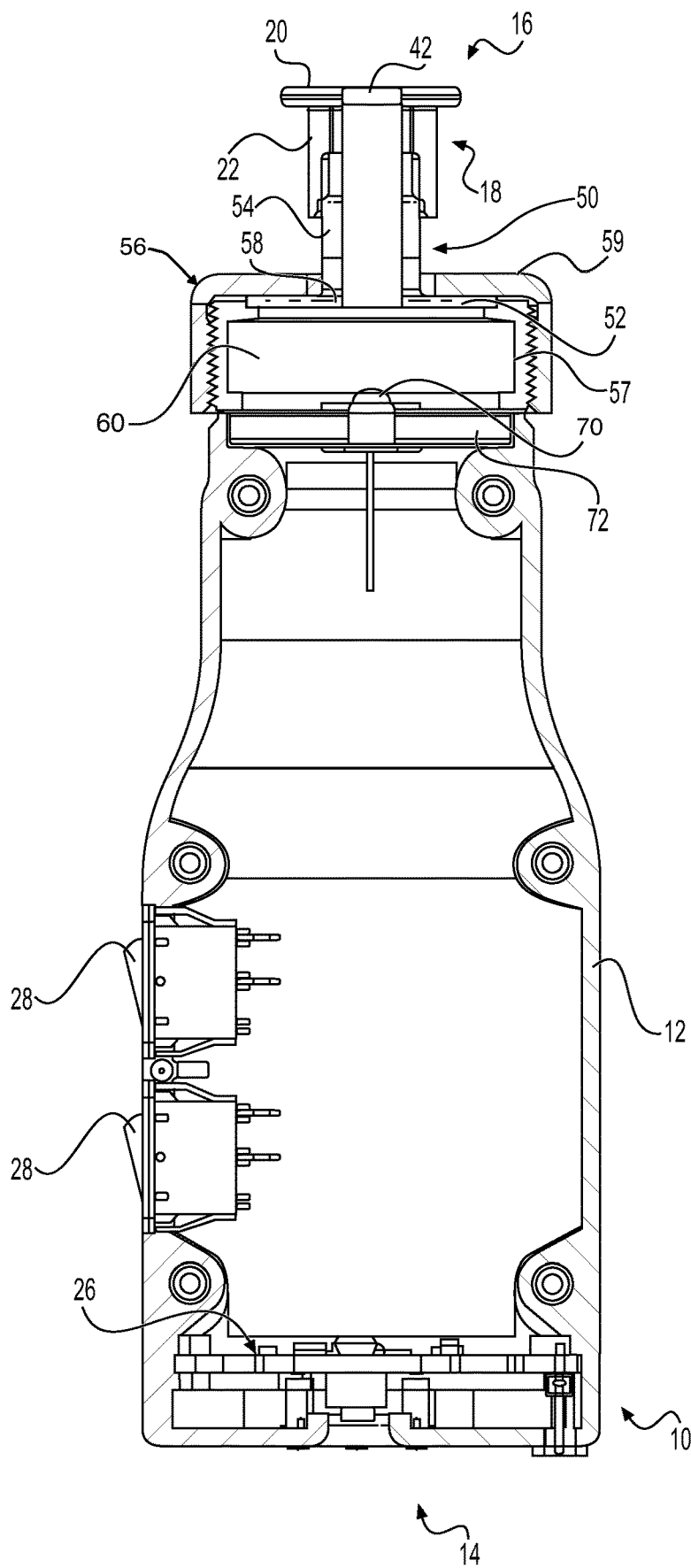
FIG. 8 is a longitudinal cross-sectional view of the device of FIG. 4 along the line A-A of FIG. 6.
Figure 9:
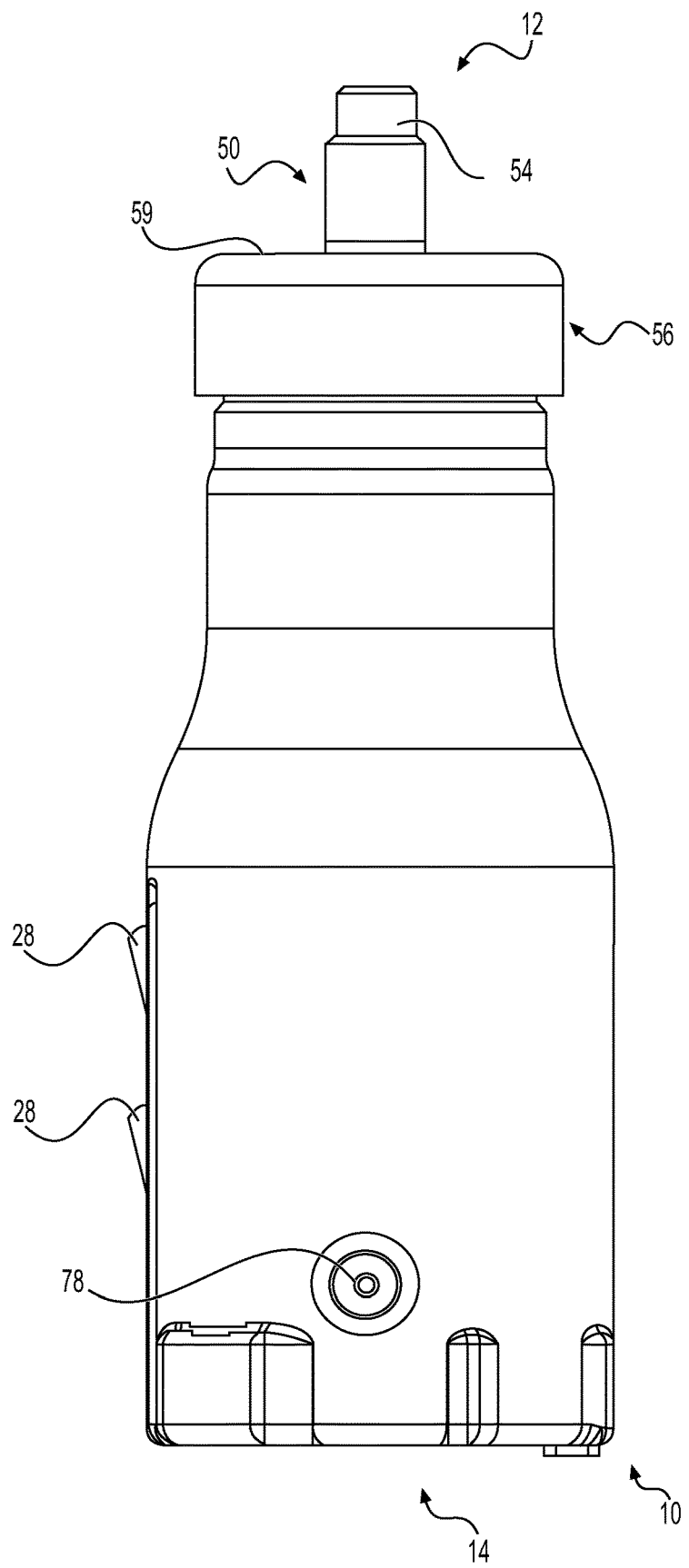
FIG. 9 is the side view of the device of FIG. 7, with an applicator removed.

Referring now to FIG. 3, the embodiment of the device 10 of FIG. 3 differs from that of FIG. 2 in that the device 10 is arranged to emit light from a light source 40 through an aperture 42 in the applicator 18. The light source 40 is operatively connected to the control unit 26. The light source 40 is configured to provide light through the aperture 42 having wavelength(s) within the electromagnetic spectrum range, for example one or more of the blue, green, orange, red and yellow parts of the electromagnetic spectrum. The light source 40 may be a light emitting diode, or a laser source. In an alternative embodiment, the light source 40 may be configured to emit light within the infra-red range of the spectrum, such as at 650-670 nm, or about 660 nm. In other embodiments, the light source 40 emits light within the ultraviolet range of the spectrum at around 200-220 nm, 220-280 nm, 270-290 nm, or 280-400 nm. Combinations of light sources 40 emitting different wavelengths are also possible. A lens (not shown) may be provided for filtering or focussing the light emitted by the light source 40 to emit the desired wavelength of light through the aperture 42.

In another embodiment (not shown), the device 10 of FIG. 3 is adapted such that the content 36 of the cartridge 34 is arranged to be supplied through the aperture 42.

A further embodiment of the device 10 is shown in FIGS. 4-9, which differs from the device 10 of FIG. 1 in that the applicator 18 is removeably attachable to the device 10. In this embodiment, the applicator 18 is a removeable tip.

The applicator body 22 is generally cylindrical in shape and defines an aperture 42 extending therethough. The applicator surface 20 is at one end of the body 24, and has a larger external diameter than the body 24. Other configurations are within the scope of the present disclosure. The applicator body 22 is made of aluminium and has a coating of silver on the applicator surface 20, as described for the device 10 of FIG. 1.

An applicator connector 50 is provided (best seen in FIG. 5), having a base portion 52 arranged to be retained in the housing 12, and an extender portion 54 extending from the base portion 52 and arranged to extend out of the housing 12 at the treatment end 16 and to connect with the applicator 18 in a male-female fashion. A longitudinal opening 55 extends through the applicator connector 50. Optionally, a portion of the extender portion 54 has insulating material extending around its circumference at the base portion 52 of the applicator connector 54. At least a portion of an external surface of the extender portion 54 and at least a portion of an internal surface of the applicator 18 are threaded to connect the applicator 18 to the applicator connector 50. In this way, the applicator 18 can be unscrewed from the applicator connector 50 to remove it from the device 10, and connected to the applicator connector 50 during use. In other embodiments, the applicator 18 is removeably connectable to the device 10 in any other way, such as by press-fit or using fasteners. The applicator 18 is reusable and can be cleaned or sterilised before each use. Alternatively, the applicator 18 can be a one-use item.

In some embodiments, the device 10 is provided with a plurality of applicators 18 (not shown) as part of a kit. In certain embodiments, the applicators 18 of the plurality of applicators 18 of the kit are the same kind as each other e.g. have substantially the same coating, the same size, and the same configuration. The applicators 18 may be used by different users, and in this respect identified by different colours or other markings. In other embodiments, the applicators 18 of the plurality of applicators 18 of the kit are different from one another e.g. they have different applicator surfaces 20 in terms of coating type, different applicator surface area, different aperture 42 size or different length. In this embodiment, these various applicators 18 can be used for different circumstances or uses. For example, a larger surface area applicator 18 can be used for larger bites or adult use, whereas a smaller surface area applicator 18 can be used on children.

A cap 56 is also provided for threaded engagement with an open end 57 of the housing 12, at the treatment end 16. The cap 56 and the housing 12 can alternatively be connected in any other way. The cap 56 defines an opening 58 extending therethrough, the opening 58 being sized and shaped to receive the extender portion 54 of the applicator connector 50. Once assembled, the applicator connector 50 is retained at the treatment end 16 of the device 10 with the extender portion 54 extending from the treatment end 16 and through the opening 58 of the cap 56. As best seen in FIGS. 6-9, the extender portion 54 is sized to space the applicator 18 from a top surface 59 of the cap 56 once the device 10 is assembled. In alternative embodiments (not shown), the extender portion 54 is sized such that the applicator 18 is flush from the top surface 59 of the cap 56. A spaced configuration may be convenient for enabling the reach of the user for uses such as on the user's feet or other hard to reach areas.

The device 10 of FIGS. 4-9 also differs from the device 10 of FIG. 1, in that the heat generation unit 24 comprises a heating plate 60 having pronged connectors 62, extending substantially perpendicular to a face 64 of the heating plate, and which are connectable to the power source 30 via a circuit (not shown). The heat generation unit 24 comprises a 1-1.5 W resistance heater. An opening 66 is defined centrally in the heating plate 60. The housing 12 includes a recess in an internal surface (not shown) for receiving the pronged connectors 62 and for holding the heat generation unit 24 in position. Once assembled, the heating plate 60 contacts the base portion 52 of the applicator connector 50 and transfers heat along the extender portion 54 to the applicator 18 connected to the extender portion 54. A thermal sensor 68 is provided for detecting the temperature of the heating plate 60. The thermal sensor 68 is connectable to the control unit 26, as well as to the heat generation unit 24. Although illustrated as two separate pieces, the heating plate 60 and the base portion 52 of the applicator connector 50 may be a single-piece.

A light emitting diode (LED) 70 is provided as the light source 40, together with a support 72 for the LED. The LED 70 is received in an opening 74 in the support 72. Once assembled, the openings 74, 66, 55, 58 and 42 are aligned and provide a light pathway. In this respect, the LED is positioned such that light emitted from the LED travels along the light pathway to be emitted from the aperture 42 of the applicator 18.

In an alternative embodiment (not shown), the device 10 is not provided with a LED 70 or LED support 72. In this embodiment, as the light pathway is not required, one or more of the applicator 18, the applicator connector 50, and the heating plate 60 do not have their respective openings or apertures 42, 55, 66.

The device 10 of FIGS. 4-9 is powered by a power connector, such as a DC power jack, connectable to an external power supply (not shown) through an opening 78 in the housing 12 at the handle end 14. In alternative embodiments (not shown) the device 10 is powered through a power source 30 housed in the device 10 such as a battery.

In an alternative embodiment (not shown), the device 10 of FIGS. 4-9 includes a cartridge port 32 for dispensing contents of a cartridge (such as the cartridge port 32 and the cartridge 34 described earlier) through the applicator 18, such as through the aperture 42.

In a yet further embodiment of the device 10 of FIGS. 4-9, an activator (not shown) is provided which is connectable to the control unit 26 through a socket (not shown) provided in the housing 12 at the handle end 14. The activator is of a plug-in form. The plug-in activator comprises a body which is connectable to the housing 12, and having on an internal surface of the body electrical connectors which extend from the body and which will operatively connect to the control unit 26 when the plug-in activator is connected to the housing 12 of the device 10. The plug-in activator comprises computer-readable instructions for instructing the control unit 26 to allow use of the device 10 for a pre-determined number of rounds of treatment. Users requiring further treatments using the device 10, will purchase additional plug-in activators, or re-charge the existing plug-in activator.

As described for the previous embodiments, the device 10 of FIGS. 4-9 and its alternative embodiments can be provided as a kit, together with replacement applicators 18 having the same or different coatings, or different antimicrobial properties. The kit can further comprise complementary treatment gels, liquids or pastes in separate containers such as anti-inflammatory, antibiotic, antiviral agent, anti-fungal agent, skin soothing, cooling, heat-activatable, wound healing, or skin rejuvenating.

In use, any of the embodiments of the device 10 can be used to administer topical treatment to a user.

In certain embodiments, the topical treatment of heat together with an antimicrobial agent has a synergistic effect. Specifically, a synergistic effect was noted with the application of heat at 54° C. and 56° C. through a silver coated applicator surface 20 (see Example). This noted effect can be applied to other synergistic agents. Without being bound to any theory, the heating of a silver coating on a metal body may accelerate silver ion release, thereby treating using heat and silver ions, and allowing an effective treatment for an array of bacterial, viral and fungal conditions at temperatures and treatment times tolerable by users. In other words, by using synergistic treatments such as heat with an antibacterial agent, an antiviral effect (against the Zika virus for example, and other virus's such as dengue virus and West Nile virus) can be achieved at a lower temperature than if an antibacterial agent was not used. For example, antiviral effect against the Zika virus can be obtained using embodiments of the present device and method by heating to up to 50-54° C. in conjunction with an application of a synergistic agent such as silver. Synergies have also been noted with agents such as one or more of silver solution, oxygenated water, oregano oil, tea tree oil, lavender oil, thyme oil, and apple cider vinegar.

In certain embodiments, the topical treatment of heat together with an antimicrobial agent has a synergistic effect in cosmetic treatments such as reducing an appearance of redness, wrinkles, or other imperfections in a user's skin.

Example

The following example is illustrative of the wide range of applicability of the present technology and is not intended to limit its scope.

The antiviral efficacy of treatments using (i) heat alone (54° C. and 56° C.), (ii) silver alone, and (iii) heat and silver, were assessed in vitro with respect to inactivation of the Zika virus (ZIKV strain PRVABC59). Treatment times of (i) 15 seconds, (ii) 30 seconds, and (iii) 45 seconds were tested. An embodiment of the device and method, as described with reference to FIGS. 4-9 and which had a silver coated tip and which could deliver heat, was used to deliver the various treatments to live Zika virus in culture media and Zika virus infected Vero cells in culture media in vitro. The tests included a negative control and a positive control (using the antiviral Ribavirin). Various concentrations of the Zika virus were used. Treatment comprised bringing the silver coated tip of the device into contact with the culture media for the stipulated treatment time. Following the in vitro treatments, virus quantification, virus viability (using Real Time-PCR), cell viability and cell proliferation were evaluated. These in vitro tests are indicative of the expected in vivo response in a human or other mammal. It was found that heat alone and silver alone had an antiviral effect. The combined heat and silver treatment were found to have a synergistic effect on the Zika virus inactivation at both temperatures tested. Based on the results, it is reasonable to extrapolate that the treatment would also be effective for other virus's such as the West Nile virus and the Dengue virus.

The present disclosure is not limited in its application to the details of construction and the arrangement of components set forth in the following description or illustrated in the drawings. The disclosure is capable of other embodiments and of being practiced or of being carried out in various ways. Also, the phraseology and terminology used herein is for the purpose of description and should not be regarded as limiting. The use of "including", "comprising", or "having", "containing", "involving" and variations thereof herein, is meant to encompass the items listed thereafter as well as, optionally, additional items. In the following description, the same numerical references refer to similar elements. The terms 'channel' and 'lumen' are used interchangeably herein.

Modifications and improvements to the above-described embodiments of the present technology may become apparent to those skilled in the art. The foregoing description is intended to be exemplary rather than limiting. The scope of the present technology is therefore intended to be limited solely by the scope of the appended claims.

What is claimed is:

1. A method for inactivating a virus, the method comprising applying a heat treatment with an antimicrobial treatment comprising uncompounded silver or copper metal, such that the virus is inactivated by the release of metal ions from the uncompounded silver or copper metal caused by heat when the heat treatment is applied.

2. The method of claim 1, wherein the heat treatment and the antimicrobial treatment is effected by applying a heated source of antimicrobial agents to an environment containing the virus.

3. The method of claim 1, wherein the virus is Zika virus, West Nile virus, or Dengue virus.

4. The method of claim 1, wherein the heat treatment comprises heating to a temperature of between 45-65° C., 50-60° C., 51-55° C. or about 51-54° C.

5. The method of claim 1, wherein the heat treatment and/or the antimicrobial treatment is applied for about 3-15 seconds, about 10-15 seconds, about 5-35 seconds, about 10-35 seconds, about 20-35 seconds, or about 25-35 seconds.

6. The method of claim 1, further comprising a light treatment.

7. The method of claim 6, wherein the light treatment is within the ultraviolet, infrared or visible range of the electromagnetic spectrum.

8. A method for treating a viral infection in a subject in need thereof, comprising topical application of a heat treatment with an antimicrobial treatment, comprising uncompounded silver or copper metal, to the subject, such that the viral infection is treated by the release of metal ions from the uncompounded silver or copper metal caused by heat when the heat treatment is applied.

9. The method of claim 8, wherein a heated source of antimicrobial agents is applied topically to the subject.

10. The method of claim 8, wherein the virus is Zika virus, West Nile virus, or Dengue virus.

11. The method of claim 9, wherein the heated source of antimicrobial agents is heated to a temperature of between 45-65° C., 50-60° C., 51-55° C. or about 51-54° C.

12. The method of claim 8, wherein the heat treatment and/or the antimicrobial treatment is applied for about 3-15 seconds, about 10-15 seconds, about 5-35 seconds, about 10-35 seconds, about 20-35 seconds, or about 25-35 seconds.

13. The method of claim 8, further comprising application of a light treatment.

14. The method of claim 13, wherein the light treatment is within the ultraviolet, infrared or visible range of the electromagnetic spectrum.

15. The method of claim 8, further comprising application of at least one agent selected from an anti-inflammatory agent, an antibiotic agent, an antiviral agent, an antifungal agent, a skin soothing agent, a cooling agent, a heat-activatable agent, a wound healing agent, and a skin rejuvenating agent.

16. The method of claim 8, wherein the heat treatment with the antimicrobial treatment is applied using a device comprising:
 a housing having a handle end and a treatment end;
 the treatment end being configured to provide an antimicrobial treatment comprising uncompounded silver or copper metal ions and a heat treatment, the treatment end comprising an applicator having an applicator surface for providing at least the heat treatment;
 a heat generation unit configured to heat the applicator surface in use;
 a source of antimicrobial agent; and
 a control unit operatively connected to at least the heat generation unit for controlling the heat generation unit.

\* \* \* \* \*